US005547675A

United States Patent [19]
Canich

[11] Patent Number: 5,547,675
[45] Date of Patent: Aug. 20, 1996

[54] MODIFIED MONOCYCLOPENTADIENYL TRANSITION METAL/ALUMOXANE CATALYST SYSTEM FOR POLYMERIZATION OF OLEFINS

[75] Inventor: Jo Ann M. Canich, Houston, Tex.

[73] Assignee: Exxon Chemical Patents Inc., Wilmington, Del.

[21] Appl. No.: 348,261

[22] Filed: Nov. 30, 1994

Related U.S. Application Data

[63] Continuation of Ser. No. 75,850, Jun. 11, 1993, abandoned, which is a continuation of Ser. No. 812,432, Dec. 23, 1991, abandoned, which is a continuation-in-part of Ser. No. 581,841, Sep. 13, 1990, Pat. No. 5,096,867, which is a continuation-in-part of Ser. No. 533,245, Jun. 4, 1990, Pat. No. 5,055,438, which is a continuation-in-part of Ser. No. 406,945, Sep. 13, 1989, abandoned.

[51] Int. Cl.$^6$ ..................... B01J 31/14
[52] U.S. Cl. .............. 502/117; 502/103; 502/118; 502/120; 502/121; 502/122; 502/123; 502/125; 502/126
[58] Field of Search ................. 502/103, 117, 502/118, 120, 121, 122, 123, 125, 126

[56] References Cited

U.S. PATENT DOCUMENTS

| | | | |
|---|---|---|---|
| 4,243,552 | 1/1981 | Welch et al. | 502/125 X |
| 4,350,802 | 9/1982 | Baba et al. | 502/125 X |
| 4,410,672 | 10/1983 | Inazawa | 502/123 X |
| 4,496,660 | 1/1985 | Gessell et al. | 502/125 X |
| 4,522,982 | 6/1985 | Ewen | 525/240 |
| 4,530,914 | 7/1985 | Ewen et al. | 502/113 |
| 4,591,577 | 5/1986 | Sato et al. | 502/123 X |
| 4,701,432 | 10/1987 | Welborn, Jr. | 502/113 |
| 4,931,517 | 6/1990 | Fujita | 526/128 |
| 5,055,438 | 10/1991 | Canich | 502/103 X |
| 5,064,802 | 11/1991 | Stevens et al. | 502/155 |
| 5,066,741 | 11/1991 | Campbell, Jr. | 502/103 |
| 5,096,867 | 3/1992 | Canich | 502/103 |
| 5,122,491 | 6/1992 | Kioka et al. | 502/117 |
| 5,132,380 | 7/1992 | Stevens et al. | 502/103 |
| 5,227,440 | 7/1993 | Canich et al. | 526/129 |

FOREIGN PATENT DOCUMENTS

| | | |
|---|---|---|
| 303519A1 | 2/1989 | European Pat. Off. |
| 406912A2 | 1/1991 | European Pat. Off. |
| 416815A2 | 3/1991 | European Pat. Off. |
| 420436A1 | 4/1991 | European Pat. Off. |
| 87/03887 | 7/1987 | WIPO |
| 93/09377 | 4/1994 | WIPO |

OTHER PUBLICATIONS

F. H. Kohler and K. H. Doll, "NMR-Spectroscopy on Paramagnetic Complexes, XXVII[1] Paramagnetic 1,1',2,2',3,3', 4,4'-Octamethylmetalbcene," Z. Naturforsch, 37b, 144–150 (1982). (month unknown).

C. M. Fendrick, et al., "Manipulation of Organoactinide Coordinative Unsaturation and Stereochemistry. Properties of Chelating Bis(polymethylcyclopentadienyl) Hydrocarbyls and Hydrides", Organometallics 1984, 3, 819–821. (month unknown).

J. Okuda, "Synthesis and Complexation of Linked Cyclopentadienyl–Amido Ligands", Chem. Ber. 123 (1990) 1649–1651 (month unknown).

Zirkonium–Organische Verbindungen, 14–24 (no date).

Hafnium–Oganische Verbindungen, 3–7 (no date).

"Study on the Preparation of Chiral Organotitanium (IV) Compounds for Enantio–Selective Synthesis", Dissertation presented by T. Kukenhohner from Detmold, School of Chemistry at the Phillips University of Marburg, Marburg (Aug. 1983).

M. T. Reetz, "Organotitanium Reagents in Organic Synthesis", Springer–Verlag, Berlin Hidelberg New York Tokyo (pp. 117 and 121) (no date).

"Organotitan (VI)–Agentien: Komplexe Chiraler Chelatiganden Und Enantioselective C–C–Verknopfungen", Inaugural–Dissertation, Thomas Kukenhohner, Detmold, 1986 (month unknown).

"Organotitanium (IV) Agents: Complexes With Chiral Chelate Ligands and Enantioselective C–C Bonds", Inaugural–Dissertation, Thomas Kukenhohner, 1986 (month unkown).

"Untersuchungen Zur Darstellung Chiraler Organotitan (IV)–Verbindungen Fur Enantioselective Synthesen" Diplomarbeit Vorgelegt von Thomas Kukenhohner aus Detmold, Aug. 1983.

Kukenhohner "Untersuchungen zur Darstellung Chiraler Organotitan (IV)–Verbindungen fur Enantioselektire Synthesen" (1983) (unpublished Diplomarbeit, University of Marburg, Germany). (month unknown).

KukenHohner, "Organotitan (IV) Agentien: Komplexe Chiraler Chelatliganden und Enantioselektire c–c– Verknupfunge" (University of Marburg, Germany 1986). (month unknown).

*Primary Examiner*—Shrive Beck
*Assistant Examiner*—Timothy H. Meeks
*Attorney, Agent, or Firm*—Charles E. Smith

[57] ABSTRACT

This invention comprises a catalyst system and a process using such catalyst system for the production of high molecular weight polyolefins, particularly polyethylene and higher poly-α-olefin, and copolymers of ethylene and/or α-olefins with other unsaturated monomers, including diolefins, acetylenically unsaturated monomers and cyclic olefins. The catalyst system comprises three components, a monocyclopentadienyl Group IV B transition metal compound, an alumoxane, and a modifier. The catalyst system is highly active, at low ratios of aluminum to the Group IV B transition metal, hence catalyzes the production of a polyolefin product containing low levels of catalyst metal residue.

20 Claims, No Drawings

MODIFIED MONOCYCLOPENTADIENYL TRANSITION METAL/ALUMOXANE CATALYST SYSTEM FOR POLYMERIZATION OF OLEFINS

This is a continuation of application Ser. No. 08/075,850, filed Jun. 11, 1993, and now abandoned, which is a continuation of application Ser. No. 07/812,432, filed Dec. 23, 1991, and now abandoned, which is a Continuation-in-Part application of U.S. patent application Ser. No. 581,841 filed Sep. 13, 1990 and now U.S. Pat. No. 5,055,438 which in turn is a Continuation-in-Part Application of U.S. patent application Ser. No. 533,245 filed Jun. 4, 1990 and now U.S. Pat. No. 5,055,438 which in turn is a Continuation-in-Part application of U.S. patent application Ser. No. 406,945 filed Sep. 13, 1989 and now abandoned.

BACKGROUND OF THE INVENTION

1. Field of the Invention

This invention relates to catalyst systems, both supported and unsupported, and to a process using such catalyst systems for the production of high molecular weight polymers, particularly polyolefins. The catalyst systems comprise a monocyclopentadienyl transition metal compound, an alumoxane, and a modifier. The catalyst system is highly active, at low ratios of aluminum to the transition metal, hence catalyzes the production of a polyolefin product containing low levels of catalyst metal residue.

2. Description of the Related Art

As is well known, various processes and catalysts exist for the homopolymerization or copolymerization of olefins. For many applications it is of primary importance for a polyolefin to have a high weight average molecular weight while having a relatively narrow molecular weight distribution. A high weight average molecular weight, when accompanied by a narrow molecular weight distribution, provides a polyolefin or an ethylene-α-olefin copolymer with high strength properties.

Traditional Ziegler-Natta catalyst systems—a transition metal compound cocatalyzed by an aluminum alkyl—are capable of producing polyolefins having a high molecular weight but the polyolefins produced thereby are generally of a broad molecular weight distribution.

More recently a catalyst system has been developed wherein the transition metal compound has two or more cyclopentadienyl ring ligands—such transition metal compound being referred to as a metallocene—which catalyzes the production of olefin monomers to polyolefins. Accordingly, metallocene compounds of a Group IV B metal, particularly, titanocenes and zirconocenes, have been utilized as the transition metal component in such "metallocene" containing catalyst system for the production of polyolefins and ethylene-α-olefin copolymers. When such metallocenes are cocatalyzed with an aluminum alkyl—as is the case with a traditional type Ziegler-Natta catalyst system—the catalytic activity of such metallocene catalyst system is generally too low to be of any commercial interest.

It has since become known that such metallocenes may be cocatalyzed with an alumoxane—rather than an aluminum alkyl—to provide a metallocene catalyst system of high activity for the production of polyolefins. A metallocene-alumoxane catalyst system generally produces polyolefins of a narrow molecular weight distribution.

The zirconium metallocene species, as cocatalyzed or activated with an alumoxane, are commonly more active than their hafnium or titanium analogous for the polymerization of ethylene alone or together with an α-olefin comonomer. When employed in a non-supported form—i.e., as a homogeneous or soluble catalyst system—to obtain a satisfactory rate of productivity even with the most active zirconium species of metallocene typically requires the use of a quantity of alumoxane activator sufficient to provide an aluminum atom (Al) to transition metal atom (TM) ratio (Al:TM) of at least greater than 1000:1; often greater than 5000:1, and frequently on the order of 10,000:1. Such quantities of alumoxane impart to a polymer produced with such catalyst system an undesirable content of catalyst metal residue, i.e., an undesirable "ash" content (the nonvolatile metal content). In high pressure polymerization procedures using soluble catalyst systems wherein the reactor pressure exceeds about 500 bar only the zirconium or hafnium species of metallocenes may be used. Titanium species of metallocenes are generally unstable at such high pressure reactor conditions unless deposited upon a catalyst support.

A wide variety of Group IV B transition metal compounds have been named as possible candidates for an alumoxane cocatalyzed catalyst system. Although bis(cyclopentadienyl) Group IV B transition metal compounds have been the most preferred and heavily investigated for use in an alumoxane activated catalyst systems for polyolefin production, suggestions have appeared that mono and tris(cyclopentadienyl) transition metal compounds may also be useful. See, for example U.S. Pat. Nos. 4,522,982; 4,530,914 and 4,701,431. Such mono(cyclopentadienyl) transition metal compounds as are suggested as candidates for an alumoxane activated catalyst system are mono(cyclopentadienyl) transition metal trihalides and trialkyls.

More recently, International Publication No. WO 87/03887 described the use of a composition comprising a transition metal coordinated to at least one cyclopentadienyl and at least one heteroatom ligand as a transition metal component for use in an alumoxane activated catalyst system for α-olefin polymerization. The composition is broadly defined as a transition metal, preferably of Group IV B of the Periodic Table, which is coordinated with at least one cyclopentadienyl ligand and one to three heteroatom ligands, the balance of the transition metal coordination requirement being satisfied with cyclopentadienyl or hydrocarbyl ligands. Catalyst systems described by this reference are illustrated solely with reference to transition metal compounds which are metallocenes, i.e., bis(cyclopentadienyl) Group IV B transition metal compounds.

Even more recently, at the Third Chemical Congress of North American held in Toronto, Canada in June 1988, John Bercaw reported upon efforts to use a compound of a Group III B transition metal coordinated to a single cyclopentadienyl heteroatom bridged ligand as a catalyst system for the polymerization of olefins. Although some catalytic activity was observed under the conditions employed, the degree of activity and the properties observed in the resulting polymer product were discouraging of a belief that such monocyclopentadienyl transition metal compound could be usefully employed for commercial polymerization processes.

U.S. Pat. No. 4,931,517 discloses a process for the polymerization of ethylene which comprises bringing ethylene, or ethylene and at least one α-olefin in contact with a catalyst comprising a metallocene compound of a transition metal selected from Groups IV B, V B and VI B, an alumoxane and a silicon compound having a Si-O-C bond for polymerization. The use of the silicon compound by the '517 patent results in the production of ethylene polymers having a lower melt flow rate due to the reduced content of the low-molecular weight matters produced.

U.S. patent application Ser. No. 406,945, now abandoned; Ser. No. 533,245, now U.S. Pat. No. 5,055,438; and Ser. No. 581,841, now U.S. Pat. No. 5,096,867 (commonly owned) and, more recently European Patent Application 416815A2 describe an alumoxane activated catalyst system for olefin polymerization wherein the transition metal component comprises a Group IV B metal atom coordinated to a single cyclopentadienyl ligand, at least one heteroatom containing ligand wherein the heteroatom and cyclopentadienyl ligand may be (and in EPO 416815A2 must be) bridged together through a bridging group containing a Group IVA or VA element, and the balance of the valence of the transition metal atom comprises univalent anionic ligands.

A need still exists for discovering catalyst systems and polymerization processes that permit the production of higher molecular weight polyolefins and desirably with a narrow molecular weight distribution. Desirably such catalyst systems should be of high activity and productivity. It is further desirable that a catalyst be discovered which, within reasonable ranges of ethylene to α-olefin monomer ratios, will catalyze the incorporation of higher contents of α-olefin comonomers in the production of ethylene-α-olefins copolymers.

SUMMARY OF THE INVENTION

A preferred catalyst system of this invention comprises a transition metal component of Group IV B metal of the Periodic Table of the Elements (*the CAS version of CRC Handbook of Chemistry and Physics*, 68th ed. 1987–1988), an alumoxane component, and a modifier. The catalyst of this invention may be employed in liquid solution, slurry, high pressure fluid, bulk, or gas phase polymerization reactors to produce a polyolefin of high weight average molecular weight and relatively narrow molecular weight distribution.

The "Group IV B transition metal component" of the catalyst system is represented by the formula:

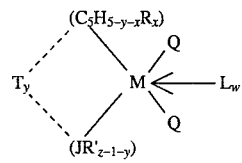

wherein: M is Zr, Hf or Ti in its highest formal oxidation state (+4, $d^0$ complex);

$(C_5H_{5-y-x}R_x)$ is a cyclopentadienyl ring and may be substituted or unsubstituted; $(JR'_{z-1-y})$ is a heteroatom ligand in which J is an element selected from Groups V A and VIA of the Periodic Table of Elements; R' may be a substituted or unsubstituted $C_1$–$C_{20}$ hydrocarbyl radical and "z" is the coordination number of the element J; each Q may be independently a univalent anionic ligand such as a halide, hydride, or substituted $C_1$–$C_{20}$ hydrocarbyl, alkoxide, aryloxide, amide, arylamide, phosphide or arylphosphide, provided that where any Q is a hydrocarbyl such Q is different from $(C_5H_{5-4-x}R_x)$; "y" is 0 or 1 when "w" is greater than 0; y is 1 when w is 0; when "y" is 1, T is a covalent bridging group containing a Group III A, IV A, V A or VIA element; and L is a neutral Lewis base.

The alumoxane component of the catalyst may be represented by the formulas: $(R^3\text{-Al-O})_m$; $R^4(R^5\text{-Al-O})_m\text{-AlR}_2^6$ or mixtures thereof, wherein $R^3$–$R^6$ are, independently, a $C_1$–$C_5$ alkyl group or halide and "m" is an integer ranging from 1 to about 50 and preferably is from about 13 to about 25.

By themselves the transition metal and alumoxane components together form an active catalyst for olefin polymerization as described in commonly-owned U.S. patent application Ser. Nos. 406,945; 533,245 and 581,841. In this invention a third component or modifier is added to the transition metal and alumoxane components to form a catalyst system of superior properties compared to that of a two component catalyst.

The addition of the modifier is important in the operation of the catalyst system of the present invention for several reasons. First, the addition of the modifier increases catalyst activity. Secondly, addition of the modifier component typically increases comonomer incorporation.

The modifier component can be represented by the formula

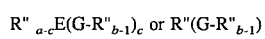

wherein G is a Group V A or VIA element and "b" is equal to the coordination number of G, E is a Group IV A or V A element and "a" is equal to the coordination number of E, "c" is an integer from 1 to 4, but not greater than "a" and each R" is independently a hydrogen, hydrocarbyl or substituted hydrocarbyl radical.

A typical polymerization process of the invention such as for the polymerization or copolymerization of ethylene comprises the steps of contacting ethylene or $C_3$–$C_{20}$ α-olefins alone, or with other unsaturated monomers including $C_3$–$C_{20}$ α-olefins, $C_4$–$C_{20}$ diolefins, and/or acetylenically unsaturated monomers either alone or in combination with other olefins and/or other unsaturated monomers, with a catalyst system comprising, a Group IV B transition metal component; a modifier; and a methylalumoxane (MAO) in an amount to provide a molar aluminum to transition metal ratio of from about 1:1 to about 20,000:1 or more; and reacting such monomer in the presence of such catalyst system at a temperature of from about –100° C. to about 300° C. for a time of from about 1 second to about 10 hours to produce a polyolefin having a weight average molecular weight of from about 1,000 or less to about 5,000,000 or more and a molecular weight distribution of from about 1.5 to about 15.0.

DESCRIPTION OF THE PREFERRED EMBODIMENT

Catalyst Component

This invention relates to a catalyst system which may be prepared in supported or unsupported form, comprising, a monocyclopentadienyl transition metal compound, an alumoxane, and a modifier. This invention further relates to a process using such catalyst systems for the production of high molecular weight polyolefins, particularly polyethylene and higher poly-α-olefins, and copolymers of ethylene and/or α-olefins with other unsaturated monomers, including diolefins, acetylenically unsaturated monomers and cyclic olefins. The catalyst system is highly active at low ratios of aluminum to the transition metal, hence catalyzes the production of a polyolefin product containing low levels of catalyst metal residue.

The transition metal compound is of the general formula

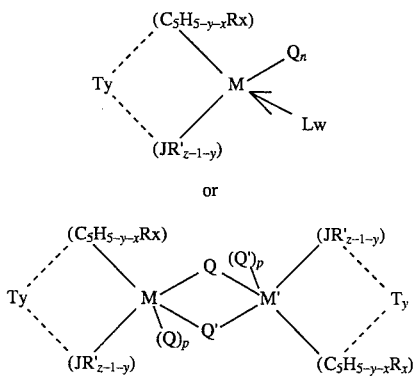

wherein M is a transition metal atom of Groups IV B, VB, VI B, $(C_5H_{5-y-x}R_x)$ is a cyclopentadienyl ligand which may be unsubstituted or substituted; $(JR'_{z-1-y})$ is a heteroatom ligand in which J is a Group V A or VIA element; the cyclopentadienyl and heteroatom ligands may be bridged together by a covalent bridging group T when "y" is 1; each Q is a univalent anionic ligand and "n+2" equals the oxidation state of M; and L is a neutral Lewis base or L can be a second transition metal compound of the sample type such that two metal centers M and M' are bridged by Q and Q', wherein M' has the same meaning as M and Q' has the same meaning as Q, and p+3 equals the oxidation state of M. Particularly preferred are bridged transition metal compounds (i.e., y=1) wherein the bridging group T is of a molecular dimension which reduces the angle defined by the bond between the heteroatom to the transition metal atom and the bond between the transition metal atom to the centroid of the cyclopentadienyl ligand from the bonding angle which would otherwise exist in an analogous compound without a bridge. The reduction of this bonding angle by such a bridging group T exposes the transition metal atom to a greater accessibility by a monomer. Illustrative, but not limiting, examples of specific T, $(C_5H_{5-y-x}R_x)$ $(JR'_{z-1-y})$ and Q constituents, are given in Table 1. Of the transition metals, Group IV B is preferred.

The Group IV B transition metal component of the catalyst system is represented by the general formula:

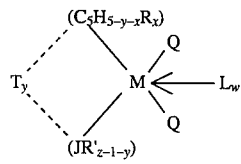

wherein M is Zr, Hf or Ti in its highest formal oxidation state (+4, $d^0$ complex);

$(C_5H_{5-y-x}R_x)$ is a cyclopentadienyl ring which is substituted with from zero to five substituent groups R, "x" is 0, 1, 2, 3, 4 or 5 denoting the degree of substitution, and each substituent group R is, independently, a radical selected from a group consisting of $C_1$–$C_{20}$ hydrocarbyl radicals, substituted $C_1$–$C_{20}$ hydrocarbyl radicals wherein one or more hydrogen atoms is replaced by a halogen radical, an amido radical, a phosphido radical, an alkoxy radical, an allylborido radical or any other radical containing a Lewis acidic or basic functionality, $C_1$–$C_{20}$ hydrocarbyl-substituted metalloid radicals wherein the metalloid is selected from the Group IV A of the Periodic Table of Elements; and halogen radicals, amido radicals, phosphido radicals, alkoxy radicals, alkylborido radicals, or any other radical containing a Lewis acidic or basic functionality, or $(C_5H_{5-y-x}R_x)$ is a cyclopentadienyl ring in which two adjacent R-groups are joined forming $C_4$–$C_{20}$ ring to give a saturated or unsaturated polycyclic cyclopentadienyl ligand such as indenyl, tetrahydroindenyl, fluorenyl or octahydrofluorenyl;

$(JR'_{z-1-y})$ is a heteroatom ligand in which J is an element with a coordination number of three from Group V A or an element with a coordination number of two from Group VIA of the Periodic Table of Elements, preferably nitrogen, phosphorus, oxygen or sulfur with nitrogen being preferred, and each R' is, independently a radical selected from a group consisting of $C_1$–$C_{20}$ hydrocarbyl radicals, substituted $C_1$–$C_{20}$ hydrocarbyl radicals wherein one or more hydrogen atoms is replaced by a halogen radical, an amido radical, a phosphido radical, an alkoxy radical, or any other radical containing a Lewis acidic or basic functionality, and "z" is the coordination number of the element J;

each Q is, independently, any univalent anionic ligand such as a halide, hydride, or substituted or unsubstituted $C_1$–$C_{20}$ hydrocarbyl, alkoxide, aryloxide, amide, arylamide, phosphide or arylphosphide, provided that where any Q is a hydrocarbyl such Q is different from $(C_5H_{5-y-x}R_x)$, or both Q together may be an alkylidene or a cyclometallated hydrocarbyl or any other divalent anionic chelating ligand;

"y" is 0 or 1 when w is greater than 0, and y is 1 when w equals 0; when "y" is 1, T is a covalent bridging group containing a Group III A, IV A, V A or VIA element such as, but not limited to, a dialkyl, alkylaryl or diaryl silicon or germanium radical, alkyl or aryl phosphine or amine radical, a hydrocarbyl radical such as methylene, ethylene and the like, an alkyl or aryl boroidoradical, or an oxygen or sulfur radical; and L is a neutral Lewis base such as diethylether, tetraethyl ammonium chloride, tetrahydrofuran, dimethylaniline, aniline, trimethylphosphine, n-butylamine, and the like; and "w" is a number from 0 to 3; L can also be a second transition metal compound of the same type such that the two metal centers M and M' are bridged by Q and Q' wherein M' has the same meaning as M and Q' has the same meaning as Q. Such compounds are represented by the formula:

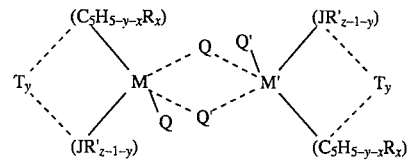

Examples of the T group which are suitable as a constituent group of the Group IV B transition metal component of the catalyst system are identified in column 1 of Table 1 under the heading "T".

Exemplary hydrocarbyl radicals for Q are methyl, ethyl, propyl, butyl, amyl, isoamyl, hexyl, isobutyl, heptyl, octyl, nonyl, decyl, cetyl, 2-ethylhexyl, phenyl and the like, with methyl being preferred. Exemplary halogen atoms for Q include chlorine, bromine, fluorine and iodine, with chlorine being preferred. Exemplary alkoxides and aryloxides for Q are methoxide, phenoxide and substituted phenoxides such as 4-methylphenoxide. Exemplary amides of Q are dimethylamide, diethylamide, methylethylamide, di-t-butylamide, diisopropylamide and the like. Exemplary aryl amides are diphenylamide and any other substituted phenyl amides. Exemplary phosphides of Q are diphenylphosphide, dicyclohexylphosphide, diethylphosphide, dimethylphosphide and the like. Exemplary alkyldiene radicals for both Q together are methylidene, ethylidene and propylidene. Examples of the Q group which are suitable as a constituent group or element of the Group IV B transition metal component of the catalyst system are identified in column 4 of Table 1 under the heading "Q".

Suitable hydrocarbyl and substituted hydrocarbyl radicals, which may be substituted as an R group for at least one hydrogen atom in the cyclopentadienyl ring, will contain from 1 to about 20 carbon atoms and include straight and branched alkyl radicals, cyclic hydrocarbon radicals, alkyl-substituted cyclic hydrocarbon radicals, aromatic radicals and alkyl-substituted aromatic radicals, alkyl-substituted aromatic radicals, amido-substituted hydrocarbyl radicals, phosphido-substituted hydrocarbyl radicals, and alkoxy-substituted hydrocarbyl radicals and cyclopentadienyl rings containing one or more fused saturated or unsaturated rings. Suitable organometallic radicals, which may be substituted as an R group for at least one hydrogen atom in the cyclopentadienyl ring, include trimethylsilyl, triethylsilyl, ethyldimethylsilyl, methyldiethylsilyl, triphenylgermyl, trimethylgermyl and the like. Other suitable radicals that may be substituted for one or more hydrogen atoms in the cyclopentadienyl ring include halogen radicals, amido radicals, phosphido radicals, alkoxy radicals, alkylborido radicals, and the like. Examples of cyclopentadienyl ring groups $(C_5H_{5-y-x}R_x)$ which are suitable as a constituent group of the Group IV B transition metal component of the catalyst system are identified in Column 2 of Table 1 under the heading $(C_5H_{5-y-x}R_x)$.

Suitable hydrocarbyl and substituted hydrocarbyl radicals, which may be substituted as an R' group for at least one hydrogen atom in the heteroatom J ligand group, will contain from 1 to about 20 carbon atoms and include straight and branched alkyl radicals, cyclic hydrocarbon radicals, alkyl-substituted cyclic hydrocarbon radicals, aromatic radicals, halogen radicals, amido radicals, phosphido radicals, and the like. Examples of heteroatom ligand groups $(JR'_{z-1-y})$ which are suitable as a constituent group of the Group IV B transition metal component of the catalyst system are identified in column 3 of Table 1 under the heading $(JR'_{z-1-y})$.

Table 1 depicts representative constituent moieties for the "Group IV B transition metal component" the list is for illustrative purposes only and should not be construed to be limiting in any way. A number of final components may be formed by permuting all possible combinations of the constituent moieties with each other. Illustrative compounds are: dimethylsilyltetramethylcyclopentadienyl-tertbutylamido zirconium dichloride, methylphenylsilyltetramethylcyclopentadienyl-tert-butylamido titanium dichloride, and dimethylsilyltetramethylcyclopentadienylcyclododecylamido titanium dichloride, and the like.

For illustrative purposes, the above compounds and those permuted from Table 1 do not include the neutral Lewis base ligand (L). The conditions under which complexes containing neutral Lewis base ligands such as ether or those which form dimeric compounds is determined by the steric bulk of the ligands about the metal center. For example, the t-butyl group in $Me_2Si(Me_4C_5)(N\text{-}t\text{-}Bu)ZrCl_2$ has greater steric requirements than the phenyl group in $Me_2Si(Me_4C_5)(NPh)ZrCl_2 \cdot Et_2O$ thereby not permitting ether coordination in the former compound. Similarly, due to the decreased steric bulk of the trimethylsilylcyclopentadienyl group in $[Me_2Si(Me_3SiC_5H_3)(N\text{-}t\text{-}Bu)ZrCl_2]_2$ versus that of the tetramethylcyclopentadienyl group in $Me_2Si(Me_4C_5)(N\text{-}t\text{-}Bu)ZrCl_2$, the former compound is dimeric and the latter is not.

TABLE 1

$$T_y\underset{(JR'_{z-1-y})}{\overset{(C_5H_{5-y-x}R_X)}{\diagdown}}M-(Q)_n$$

| T (when y = 1) | $(C_5H_{5-y-x}R_x)$ | $(JR'_{z-1-y})$ | Q | M |
|---|---|---|---|---|
| dimethylsilyl | cyclopentadienyl | t-butylamido | hydride | zirconium |
| diethylsilyl, oxygen | methylcylcopentadienyl | phenylamido | chloro | hafnium |
| di-n-propylsilyl, sulfur | 1,2-dimethylcyclopentadienyl | p-n-butylphenylamido | methyl | titanium |
| diisopropylsilyl | 1,3-dimethylcyclopentadienyl | cyclohexylamido | ethyl | |
| di-n-butylsilyl | idenyl | perfluorophenylamido | phenyl | Group: |
| di-t-butylsilyl | 1,2-diethylcyclopentadienyl | n-butylamido | fluoro | III B |
| di-n-hexylsilyl | tetramethylcyclopentadienyl | methylamido | bromo | IV B |
| methylphenylsilyl | ethylcyclopentadienyl | ethylamido | iodo | V B |
| ethylmethylsilyl | n-butylcyclopentadienyl | n-propylamido | n-propyl | VI B |
| diphenylsilyl | cyclohexylmethylcyclopentadienyl | isopropylamido | isopropyl | VII B |
| di(p-t-butylphenethylsilyl) | n-octylcyclopentadienyl | benzylamido | n-butyl | VIII B |
| n-hexylmethylsilyl | β-phenylpropylcyclopentdienyl | t-butylphosphido | | |
| cyclopentamethylenesilyl | tetrahydroindenyl | ethylphosphido | | Lantha- |
| cyclotetramethylenesilyl | propylcyclopentadienyl | phenylphosphido | | nide |
| cylyclotrimethylenesilyl | t-butylcyclopentadienyl | cyclohexylphosphido | | |
| dimethylgermanyl | benzylcyclopentadienyl | oxo (when y = 1) | | |
| diethylgermanyl | diphenylmethylcyclopentadienyl | sulfido (when y = 1) | | |
| phenylamido | trimethylgermylcyclopentadienyl | methoxide (when y = 0) | | |
| t-butylamido | trimethylstannylcyclopentadienyl | ethyoxide (when y = 0) | | |
| methylamido | triethylplumbylcyclopentadienyl | methylthio (when y 0) | | |
| t-butylphosphido | trifluoromethylcyclopentadienyl | ethylthio (when y = 0) | | |
| ethylphosphido | trimethylsilylcyclopentadienyl | | | |
| phenylphosphido | pentmethylcyclopentadienyl (when y = 0) | | | |
| methylene | fluorenyl | | | |
| dimethylmethylene | octahydrofluorenyl | | | |
| diethylmethylene | 1,2,4-trimethylcyclopentadienyl | | | |
| ethylene | 1-t-butyl-3- | | | |
| dimethylethylene | trimethylsilylcyclopentadienyl | | | |
| diethylethylene | diphenylboridocyclopentadienyl | | | |

TABLE 1-continued $$T_y \overset{(C_5H_{5-y-x}R_x)}{\underset{(JR'_{z-1-y})}{M-(Q)_n}}$$

| T (when y = 1) | $(C_5H_{5-y-x}R_x)$ | $(JR'_{z-1-y})$ | Q | M |
|---|---|---|---|---|
| dipropylethylene | dimethylamidocyclopentadienyl | | | |
| propylene | diphenylphosphidocyclopentadienyl | | | |
| dimethylpropylene | methoxycyclopentadienyl | | | |
| diethylpropylene | | | | |
| 1,1-dimethyl-3,3-dimethylpropylene | | | | |
| tetramethyldisiloxane | | | | |
| 1,1,4,4-tetramethyldisilylethylene | | | | |
| phenyl borido | | | | |
| ethyl borido | | | | |

Generally the bridged species of the Group IV B transition metal compound ("y"=1) are preferred. These compounds can be prepared by reacting a cyclopentadienyl lithium compound with a dihalo compound whereupon a lithium halide salt is liberated and a monohalo substituent is covalently bound to the cyclopentadienyl compound. The so substituted cyclopentadienyl reaction product is next reacted with a lithium salt of a phosphide, oxide, sulfide or amide (for the sake of illustrative purposes, a lithium amide) whereupon the halo element of the monohalo substituent group of the reaction product reacts to liberate a lithium halide salt and the amine moiety of the lithium amide salt is covalently bound to the substituent of the cyclopentadienyl reaction product. The resulting amine derivative of the cyclopentadienyl product is then reacted with an alkyl lithium reagent whereupon the labile hydrogen atoms, at the carbon atom of the cyclopentadienyl compound and at the nitrogen atom of the amine moiety covalently bound to the substituent group, react with the alkyl of the lithium alkyl reagent to liberate the alkane and produce a dilithium salt of the cyclopentadienyl compound. Thereafter the bridged species of the Group IV B transition metal compound is produced by reacting the dilithium salt cyclopentadienyl compound with a Group IV B transition metal preferably a Group IV B transition metal halide.

Unbridged species of the Group IV B transition metal compound can be prepared from the reaction of a cyclopentadienyl lithium compound and a lithium salt of an amine with a Group IV B transition metal halide.

Suitable, but not limiting, Group IV B transition metal compounds which may be utilized in the catalyst system of this invention include those bridged species ("y"=1) wherein the T group bridge is a dialkyl, diaryl or alkylaryl silane, or methylene or ethylene. Exemplary of the more preferred species of bridged Group IV B transition metal compounds are dimethylsilyl, methylphenylsilyl, diethylsilyl, ethylphenylsilyl, diphenylsilyl, ethylene or methylene bridged compounds. Most preferred of the bridged species are dimethylsilyl, diethylsilyl and methylphenylsilyl bridged compounds.

Suitable Group IV B transition metal compounds which are illustrative of the unbridged ("y"=0) species which may be utilized in the catalyst systems of this invention are exemplified by pentamethylcyclopentadienyldi-t-butylphosphinodimethyl hafnium; pentamethylcyclopentadienyldi-t-butylphosphinomethylethyl hafnium; cyclopentadienyl-2-methylbutoxide dimethyl titanium.

To illustrate members of the Group IV B transition metal component, select any combination of the species in Table 1.

An example of a bridged species would be dimethylsilylcylclopentadienyl-t-butylamidodichloro zirconium; an example of an unbridged species would be cyclopentadienyldi-t-butylamidodichloro zirconium.

Generally, wherein it is desired to produce an α-olefin copolymer which incorporates a high content of α-olefin, the species of Group IV B transition metal compound preferred is one of titanium. The most preferred species of titanium metal compounds are represented by the formula:

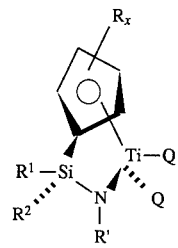

wherein Q, L, R', R, "x" and "w" are as previously defined and $R^1$ and $R^2$ are each independently a $C_1$ to $C_{20}$ hydrocarbyl radicals, substituted $C_1$ to $C_{20}$ hydrocarbyl radicals wherein one or more hydrogen atom is replaced by a halogen atom; $R^1$ and $R^2$ may also be joined forming a $C_3$ to $C_{20}$ ring which incorporates the silicon bridge.

The alumoxane component of the catalyst system is an oligomeric compound which may be represented by the general formula $(R^3\text{-Al-O})_m$ which is a cyclic compound, or may be $R^4(R^5\text{-Al-O-})_m\text{-AlR}_2^6$ which is a linear compound. An alumoxane is generally a mixture of both the linear and cyclic compounds. In the general alumoxane formula $R^3$, $R^4$, $R^5$ and $R^6$ are, independently a $C_1$–$C_5$ alkyl radical, for example, methyl, ethyl, propyl, butyl or pentyl and "m" is an integer from 1 to about 50. Most preferably, $R^3$, $R^4$, $R^5$ and $R^6$ are each methyl and "m" is at least 4. When an alkyl aluminum halide is employed in the preparation of the alumoxane, one or more $R^{3-6}$ groups may be halide.

As is now well known, alumoxanes can be prepared by various procedures. For example, a trialkyl aluminum may be reacted with water, in the form of a moist inert organic solvent; or the trialkyl aluminum may be contacted with a hydrated salt, such as hydrated copper sulfate suspended in an inert organic solvent, to yield an alumoxane. In another method wherein a supported form of catalyst is desired, a non-dehydrated or wet gel, such as a wet silica gel may be reacted with a trialkyl aluminum to prepare the alumoxane in situ on the support. Generally, however prepared, the reaction of a trialkyl aluminum with a limited amount of water yields a mixture of both linear and cyclic species of alumoxane.

Suitable alumoxanes which may be utilized in the catalyst systems of this invention are those prepared by the hydrolysis of a trialkylaluminum; such as trimethylaluminum, triethylaluminum, tripropylaluminum; triisobutylaluminum, dimethylaluminumchloride, diisobutylaluminumchloride, diethylaluminumchloride, and the like. The most preferred alumoxane for use is methylalumoxane (MAO). Methylalumoxanes having an average degree of oligomerization of from about 4 to about 25 ("m"=4 to 25), with a range of 13 to 25, are the most preferred.

Generally, the modifier component is a Lewis base or a compound containing one or more Lewis basic functionalities which are capable of reacting with a Lewis acid such as trimethylaluminum. Such modifiers are represented by, but not limited to N,N-dimethylanaline, ethylamine, diethylamine, triethylamine, triphenylamine, triphenylphosphine, hexamethylphosphorous triamide, diethylether, water, deuterium oxide, ethanol, phenol, thiophenol, 2,6-di-t-butyl-4-methylphenol, tetraethoxysilane, phenyltriethoxysilane, diphenyldiethoxysilane, triphenylethoxysilane, diethyldihydroxysilane and the like. The modifier component can be represented by the formula:

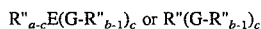

$$R''_{a-c}E(G-R''_{b-1})_c \text{ or } R''(G-R''_{b-1})_c$$

wherein G is a Group V A or VIA element and "b" is equal to the coordination number of G, E is a Group IV A or V A element and "a" is equal to the coordination number of E, "c" is an integer from 1 to 4, and each R" is independently a hydrogen, hydrocarbyl or substituted hydrocarbyl radical. Likewise, dimeric, trimeric, tetrameric or oligomeric versions of these compounds could be used. Examples of such compounds include N,N,N',N'-tetramethylethylenediamine, 2 2',2"-triaminotriethylamine, hexamethylenetetraamine, 1,4,7,10,13,16-hexamethyl-1,4,7,10,13,16-hexaazacyclooctadecane, 1,2-bis(diphenylphosphino)ethane, tris(2-diphenylphosphinoethyl)phosphine, -1,1,1-tris(diphenylphosphinomethyl)ethane, 4,7,13,16,21,24-hexaoxa- 1,10-diazabicyclo[8.8.8]hexacosane, 12-crown- 4,15-crown-5, 18-crown-6, 1,4,7,10,13,16-hexathiacyclooctadecane, hexamethylcyclotrisiloxane, and the like.

The catalyst system in soluble unsupported form is prepared by comixing the transition metal compound, alumoxane and modifier component in any order of addition or simultaneously in a hydrocarbon solvent which, preferably is suitable for use as a polymerization diluent.

Where the hydrocarbon solvent utilized is also suitable for use as a polymerization diluent, the catalyst system may be prepared in situ in the polymerization reactor. Alternatively, the catalyst system may be separately prepared, in concentrated form, and added to the polymerization diluent in a reactor. Or, if desired, the components of the catalyst system may be prepared as separate solutions and added to the polymerization diluent in a reactor, in appropriate ratios, as is suitable for a continuous liquid phase polymerization reaction procedure. Alkane and aromatic hydrocarbons suitable as solvents for formation of the catalyst system and also as a polymerization diluent are exemplified by, but are not necessarily limited to, straight and branched chain hydrocarbons such as isobutane, butane, pentane, hexane, heptane, octane and the like, cyclic and alicyclic hydrocarbons such as cyclohexane, cycloheptane, methylcyclohexane, methylcycloheptane and the like, and aromatic and alkyl-substituted aromatic compounds such as benzene, toluene, xylene and the like. Suitable solvents also include liquid olefins which may act as monomers or comonomers including ethylene, propylene, 1-butene, 1-hexene and the like.

The transition metal compound and alumoxane are employed in quantities such that the transition metal compound is present in solution in a concentration of from about 0.00001 to about 1.0 millimoles/liter and the alumoxane is present in an amount to provide a ratio of aluminum atom to transition metal atom of from about 1:1 to about 20,000:1. The modifier is employed in an amount to provide a mole ratio of modifier to transition metal compound of from about 1:1 to about 5,000:1.

The catalyst system ingredients—that is, the Group IV B transition metal, the alumoxane, the modifier and polymerization diluent (optional)—can be added to the reaction vessel rapidly or slowly. The temperature maintained during the contact of the catalyst components can vary widely, such as, for example, from −100° to 300° C. Greater or lesser temperatures can also be employed. Preferably, during formation of the catalyst system, the reaction is maintained within a temperature of from about 25° to 100° C., most preferably about 25° C.

At all times, the individual catalyst system components, as well as the catalyst system once formed, are protected from oxygen and moisture. Therefore, the reactions to prepare the catalyst system are performed in an oxygen and moisture free atmosphere and, where the catalyst system is recovered separately it is recovered in an oxygen and moisture free atmosphere. Preferably, therefore, the reactions are performed in the presence of an inert dry gas such as, for example, helium or nitrogen.

If desired the catalyst may also be prepared in a supported form. The normally hydrocarbon soluble transition metal component and alumoxane are prepared as a supported catalyst by deposition on a support material. The modifier may also be, and preferably is, deposited on a support or the modifier may be used in conjunction with a supported transition metal compound-alumoxane/component by addition of the modifier to a polymerization diluent to which the supported transition metal compound alumoxane component is ultimately added. The support material for preparing the supported catalyst may be any resinous support material such as a polyolefin or any finely divided inorganic solid porous support, such as talc, silica, alumina, silica-alumina, or mixtures thereof. Other inorganic oxides that may be employed either alone or in combination with silica or silica alumina are magnesia, titania, zirconia, and the like. The inorganic oxides may be dehydrated, as is well known in the art, to remove water. If desired, the residual surface hydroxyl groups in the inorganic solid porous support may be removed by additional heating or by reaction with chemical dehydrating agents such as lithium alkyl, silylchlorides, aluminum alkyls, or preferably with alumoxane. Preferred catalyst supports include dehydrated inorganic oxide treated with an alumoxane, more preferably with methylalumoxane. A suitable support material of this type is a dehydrated silica gel treated with methylalumoxane. When such a alumoxane-treated support is utilized in the production of the supported catalyst, it may not be necessary to include additional alumoxane in the catalyst composition. Also preferred as a catalyst support is a wet gel, more preferably a wet silica gel, containing up to approximately 20% by weight absorbed water. Wet gels may be directly mixed with trialkyl aluminums to form the alumoxane component of the catalyst system directly on the support.

A suitable inorganic support such as silica would have a particle diameter in the range of 0.1–600 microns, preferably 0.3–100 microns; a surface area of 50–1000 m²/g, preferably 100–500 m²/g; and a pore volume of 0.5–3.5 cm³/g. To insure its use in dehydrated form, the support material may be heat treated at 100°–1000° C. for a period of 1–100 hours, preferably 3–24 hours. The treatment may be carried out in a vacuum or while purging with a dry inert gas such as nitrogen. As an alternative, the support material may be chemically dehydrated. The chemical dehydration is accomplished by slurrying the support in an inert low boiling solvent such as, for example, heptane, in the presence of the dehydrating agent such as for example, triethylaluminum in a moisture and oxygen-free atmosphere.

Method of Use

The catalyst system may be most usefully employed in liquid, solution, slurry, high pressure fluid, bulk or gas phase processes, all of which are known to those of skill in the art. These processes may be employed singularly or in series. Thus, polymerizations using the invention catalyst system may be conducted by any of these processes, generally at a temperature in the range of about 0° to about 220° C. or even higher, and under atmospheric, subatmospheric or superatmospheric pressure conditions.

A slurry polymerization process can utilize sub- or superatmospheric pressures and temperatures in the range of –80 to 250° C. In a slurry polymerization, a suspension of solid, particulate polymer is formed in a liquid polymerization medium to which ethylene, α-olefin, diolefin, cyclic olefin or acetylenically unsaturated comonomer, hydrogen (optional) and catalyst are added. Alkanes and cycloalkanes, such as butane, pentane, hexane, or cyclohexane, are preferred with $C_4$ to $C_{20}$ alkanes especially preferred. Preferred solvents also include liquid olefins which may act as monomers or comonomers including ethylene, propylene, butadiene, cyclopentene, 1-hexene, 3-methyl-1-pentene, 4-methyl-1-pentene, 1,4-hexadiene, 1-octene, 1-decene, styrene, substituted styrenes and the like.

A gas-phase polymerization process utilizes superatmospheric pressure and temperatures in the range of about 50° C.–120° C. Gas-phase polymerization can be performed in a stirred or fluidized bed of catalyst and product particles in a pressure vessel adapted to permit the separation of product particles from unreacted gases. Thermostated ethylene, comonomer, including α-olefins, diolefins, cyclic olefins or acetylenically unsaturated comonomer, hydrogen and an inert diluent gas such as nitrogen can be introduced or recirculated so as to maintain the particles at a temperature of 50°–120° C. The polymer product can be withdrawn continuously or semi-continuously at a rate such as to maintain a constant product inventory in the reactor. After polymerization and deactivation of the catalyst, the product polymer can be recovered by any suitable means. In commercial practice, the polymer product can be recovered directly from the gas phase reactor, freed of residual monomer with a nitrogen purge, and used without further deactivation or catalyst removal.

The liquid phase process comprises the steps of contacting an olefin monomer with the catalyst system in a suitable polymerization diluent and reacting said monomer in the presence of said catalyst system for a time and at a temperature sufficient to produce a polyolefin of high molecular weight.

The monomer for such process may comprise ethylene alone, for the production of a homopolyethylene, or ethylene in combination with an α-olefin having 3 to 20 carbon atoms for the production of an ethylene-α-olefin copolymer. Homopolymers of higher α-olefin such as propylene, butene, styrene and copolymers thereof with ethylene and/or $C_4$ or higher α-olefins and diolefins can also be prepared. Conditions most preferred for the homo- or copolymerization of ethylene are those wherein ethylene is submitted to the reaction zone at pressures of from about 0.019 psia to about 50,000 psia and the reaction temperature is maintained at from about -100° to about 300° C. The aluminum to transition metal molar ratio is preferably from about 1:1 to 20,000 to 1. A more preferable range would be 1:1 to 2000:1. The reaction time is preferably from about 10 seconds to about 1 hour. Without limiting in any way the scope of the invention, one means for carrying out the process of the present invention for production of a copolymer is as follows: in a stirred-tank reactor liquid α-olefin monomer is introduced, such as 1-butene. The catalyst system is introduced via nozzles in either the vapor or liquid phase. Feed ethylene gas is introduced either into the vapor phase of the reactor, or sparged into the liquid phase as is well known in the art. The reactor contains a liquid phase composed substantially of liquid α-olefin comonomer, together with dissolved ethylene gas, and a vapor phase containing vapors of all monomers. The reactor temperature and pressure may be controlled via reflux of vaporizing α-olefin monomer (autorefrigeration), as well as by cooling coils, jackets etc. The polymerization rate is controlled by the concentration of catalyst. The ethylene content of the polymer product is determined by the ratio of ethylene to α-olefin comonomer in the reactor, which is controlled by manipulating the relative feed rates of these components to the reactor.

While it is a characteristic of the catalyst system that the produced polymers have a narrow molecular weight distribution, if desired broad molecular weight distribution polymers may be produced by using two or more transition metal compounds or two or more activators.

The invention is illustrated in actual practice by the following non-limiting examples.

EXAMPLES

All procedures were performed under an inert atmosphere of helium or nitrogen. Solvent choices are often optional, for example, in most cases either pentane or 30–60 petroleum ether can be interchanged. The lithiated amides were prepared from the corresponding amines and either n-BuLi or MeLi. Published methods for preparing $LiHC_5Me_4$ include C. M. Fendrick et al. *Organometallics*, 3, 819 (1984) and F. H. Köhler and K. H. Doll, *Z. Naturforich*, 376, 144 (1982). Other lithiated substituted cyclopentadienyl compounds are typically prepared from the corresponding cyclopentadienyl ligand and n-BuLi or MeLi, or by reaction of MeLi with the proper fulvene. $TiCl_4$ was purchased from either Aldrich Chemical Company or Cerac. $TiCl_4$ was typically used in its etherate form. The etherate, $TiCl_4 \cdot 2Et_2O$, can be prepared by gingerly adding $TiCl_4$ to diethylether. Amines, silanes and lithium reagents were purchased from Aldrich Chemical Company or Petrarch Systems. Methylalumoxane was supplied by either Schering or Ethyl Corp.

Part 1. $MePhSiCl_2$ (14.9 g, 0.078 mol) was diluted with 250 ml of thf. $Me_4HC_5Li$ (10.0 g, 0.078 mol) was slowly added as a solid. The reaction solution was allowed to stir overnight. The solvent was removed via a vacuum to a cold trap held at –196° C. Petroleum ether was added to precipitate the $LiC_1$. The mixture was filtered through Celite and the pentane was removed from the filtrate. $MePhSi(Me_4C_5H)Cl$ (20.8 g, 0.075 mol) was isolated as a yellow viscous liquid.

Part 2. LiHN-t-Bu (4.28 g, 0.054 mol) was dissolved in ~100 ml of thf. MePhSi(C$_5$Me$_4$H)Cl (15.0 g, 0.054 mol) was added dropwise. The yellow solution was allowed to stir overnight. The solvent was removed in vacuo. Petroleum ether was added to precipitate the LiCl. The mixture was filtered through Celite, and the filtrate was evaporated. MePhSi(C$_5$Me$_4$H)(NH-t-Bu) (16.6 g, 0.053 mol) was recovered as an extremely viscous liquid.

Part 3. MePhSi(C$_5$Me$_4$H)(NH-t-Bu) (17.2 g, 0.055 mol) was diluted with ~20 ml of ether. n-BuLi (60 ml in hexane, 0.096 mol, 1.6M was slowly added and the reaction mixture was allowed to stir for ~3 hours. The solvent was removed in vacuo to yield 15.5 g (0.48 mol) of a pale tan solid formulated as Li$_2$[MePhSi(C$_5$Me$_4$)(N-t-Bu)].

Part 4. Li$_2$ [MePhSi (C$_5$Me$_4$) (N-t-Bu)] (8.75 g, 0. 027 mol) was suspended in ~125 ml of cold ether (−30° C.). TiCl$_4$.2Et$_2$O(9.1 g, 0.027 mol) was slowly added. The reaction was allowed to stir for several hours prior to removing the ether via vacuum. A mixture of toluene and dichloromethane was then added to solubilize the product. The mixture was filtered through Celite to remove the LiCl. The solvent was largely removed via vacuum and petroleum ether was added. The mixture was cooled to maximize product precipitation. The crude product was filtered off and redissolved in toluene. The toluene insolubles were filtered off. The toluene was then reduced in volume and petroleum ether was added. The mixture was cooled to maximize precipitation prior to filtering off 3.34 g (7.76 mmol) of the yellow solid MePhSi(C$_5$Me$_4$)(N-t-Bu)TiCl$_2$.

The examples are all based on the transition metal compound (MePhSi(Me$_4$C$_5$) (N-t-Bu)TiCl$_2$) with methylalumoxane (MAO).

The examples are collected in Table II. The general procedure is the same for all the runs. The codes to the modifiers is as follows: BHT (2,6-di-t-butyl-4-methylphenol), DMA (N,N-dimethylanaline), TEOS (tetraethoxysilane), DPDEOS (diphenyldiethoxysilane), and PTEOS (phenyltriethoxysilane). Trimethylaluminum is abbreviated as TMA and is provided as a counter example. Methylalumoxane is abbreviated as MAO. MW is weight average molecular weight, MWD is molecular weight distribution, and short chain branching per 1000 carbon atoms (SCB/1000C) was determined by either IR(a), $^1$H NMR (b) or $^{13}$C NMR (c).

Polymerization

General Catalyst Preparation and Polymerization Procedure

The polymerization run was performed in a 1-liter autoclave reactor equipped with a paddle stirrer, an external water jacket for temperature control, a regulated supply of dry nitrogen, ethylene, propylene, 1-butene and hexane, and a septum inlet for introduction of other solvents or comonomers, transition metal compound and alumoxane solutions. The reactor was dried and degassed thoroughly prior to use. A typical run consisted of injecting into the reactor 300 ml of toluene, 100 ml of 1-butene, the specified amount of 1.0 M methylalumoxane (MAO) which had been mixed with the specified modifier (MOD), and 1 ml of a toluene solution of the transition metal compound. Exact amounts are collected in Table II. The reactor was then heated to 80° C. and the ethylene (65 psi) was introduced into the system. The polymerization reaction was limited to the specified time (30 to 35 minutes). The reaction was ceased by rapidly cooling and venting the system and the ethylene-butene copolymer was recovered and allowed to dry under a stream of nitrogen.

The invention has been described with reference to its preferred embodiments. Those of ordinary skill in the art may, upon reading this disclosure, appreciate changes or modifications which do not depart from the scope and spirit of the invention as described above or claimed hereafter.

TABLE II

| A<br>Exp # | C<br>Modifier | D<br>mmol TM | E<br>mmol MAO | F<br>mmol Mod | G<br>Al/Tm (mol) | H<br>Al/MOD (mol) |
| --- | --- | --- | --- | --- | --- | --- |
| 1 | None | 0.00244 | 7.5 | | 3074 | |
| 2 | BHT | 0.00244 | 7.5 | 0.00908 | 3074 | 826 |
| 3 | BHT | 0.00244 | 7.5 | 0.01815 | 3074 | 413 |
| 4 | DMA | 0.00302 | 5.0 | 0.01271 | 1656 | 393 |
| 5 | DMA | 0.00304 | 7.5 | 0.25747 | 2467 | 29 |
| 6 | TEOS | 0.00302 | 7.5 | 0.0192 | 2483 | 391 |
| 7 | DPDEOS | 0.00302 | 7.5 | 0.01652 | 2483 | 454 |
| 8 | PTEOS | 0.00321 | 4.0 | 0.0208 | 1248 | 192 |
| 9 | TMA | 0.00302 | 4.0 | 0.02774 | 1325 | 144 |
| 10 | TMA | 0.00302 | 6.0 | 0.02774 | 1987 | 216 |

| Exp. | I<br>Mod/TM (mol) | J<br>T (C) | K<br>P (psi) | L<br>C$_4$ (ml) | M<br>t (hr) | N<br>Mw | O<br>MWD | P<br>SCB/1000 C | Q<br>Yield (g) |
| --- | --- | --- | --- | --- | --- | --- | --- | --- | --- |
| 1 | | 80 | 60 | 100 | 0.58 | 87,900 | 2.122 | 55.5(a) | 35.0 |
| 2 | 3.2 | 80 | 65 | 100 | 0.5 | 71,700 | 2.254 | 57.0(a) | 46.7 |
| 3 | 7.44 | 80 | 65 | 100 | 0.5 | 55,600 | 2.159 | 66.0(a) | 41.9 |
| 4 | 4.21 | 80 | 65 | 100 | 0.5 | 72,600 | 2.308 | 154.2(c) | 91.6 |
| 5 | 84.69 | 80 | 65 | 100 | 0.5 | 81,600 | 1.913 | 133.0(b) | 86.8 |
| 6 | 6.36 | 80 | 65 | 100 | 0.5 | 77,800 | 2.043 | 146.0(b) | 97.9 |
| 7 | 5.47 | 80 | 65 | 100 | 0.5 | 95,900 | 1.900 | 86.6(a) | 42.6 |
| 8 | 6.49 | 80 | 65 | 100 | 0.5 | 26,600 | 3.150 | 71.0(b) | 130.4 |
| 9 | 9.19 | 80 | 65 | 100 | 0.5 | 40,100 | 3.460 | 131.1(c) | 23.6 |
| 10 | 9.19 | 80 | 65 | 100 | 0.58 | 64,800 | 3.557 | 91.6(a) | 27.6 |

I claim:

1. A catalyst system comprising:

(A) a transition metal compound or lanthanide metal compound of the formula:

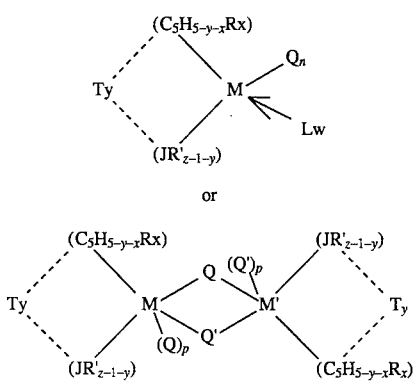

wherein
- M is a transition metal or lanthanide metal atom;
- $(C_5H_{5-y-x}R_x)$ is a cyclopentadienyl ring which is substituted with from zero to five substituent groups R, "x" is 0, 1, 2, 3, 4 or 5 denoting the degree of substitution, and each substituent group R is, independently, a radical selected from the group consisting of $C_1$–$C_{20}$ hydrocarbyl radicals; substituted $C_1$–$C_{20}$ hydrocarbyl radicals wherein one or more hydrogen atoms is replaced by a halogen radical, an amido radical, a phosphido radical, an alkoxy radical, an alkylborido radical, or other radical containing a Lewis acidic or basic 18 functionality; $C_1$–$C_{20}$ hydrocarbyl-substituted metalloid radicals wherein the metalloid is selected from the Group IV A of the Periodic Table of Elements; halogen radicals; amido radicals; phosphido radicals; alkoxy radicals; alkylborido radicals; and other radical containing Lewis acidic or basic functionality; or $(C_5H_{5-y-x}R_x)$ is a cyclopentadienyl ring in which two adjacent R-groups are joined forming $C_4$–$C_{20}$ ring to give a saturated or unsaturated polycyclic cyclopentadienyl ligand;
- $(JR'_{z-1-y})$ is a heteroatom ligand in which J is an element with a coordination number of three from Group V A or an element with a coordination number of two from Group VIA of the Periodic Table of Elements, each R' is, independently a radical selected from the group consisting of $C_1$–$C_{20}$ hydrocarbyl radicals and substituted $C_1$–$C_{20}$ hydrocarbyl radicals wherein one or more hydrogen atom is replaced by a halogen radical, an amido radical, a phosphido radical, an alkoxy radical, an alkylborido radical, or a radical containing a Lewis acidic or basic functionality; and "z" is the coordination number of the element J;
- each Q is, independently, an univalent anionic ligand selected from the group consisting of halide, hydride, a substituted or unsubstituted $C_1$–$C_{20}$ hydrocarbyl, alkoxide, aryloxide, amide, and phosphide provided that where Q is a hydrocarbyl ligand Q cannot be a substituted or unsubstituted cyclopentadienyl ring or both Q together are an alkylidene, a cyclometallated hydrocarbyl or a divalent anionic chelating ligand;
- "n" and "p" are integer numbers such that n+2 and p+3 are equal to the oxidation state of M and the oxidation state of M is 3 or greater;
- "y" is 0 or 1 when "w" is greater than 0; "y" is 1 when "w" is 0; when "y" is 1, T is a covalent bridging group containing a Group III A, IV A, V A, or VIA element;
- L is a neutral Lewis base where "w" denotes a number from 0 to 3; and (B) an alumoxane; and (C) a modifier of the formula $$R''_{a-c}E(G-R''_{b-1})_c \text{ or } R''(G-R''_{b-1})$$

wherein G is a Group VA or VIA element and "b" is equal to the coordination number of G, E is a Group IVA or VA element and "a" is equal to the coordination number of E, "c" is an integer from 1 to 4 but not greater than "a", and each R" is independently a hydrogen, hydrocarbyl or substituted hydrocarbyl radical.

2. The catalyst system of claim 1, wherein the transition metal atom is from Group IV B, V B, or VI B of the Periodic Table of the Elements.

3. The catalyst system of claim 2, wherein M is Zr, Hf of Ti in its highest formal oxidation state and the transition metal compound is of the formula

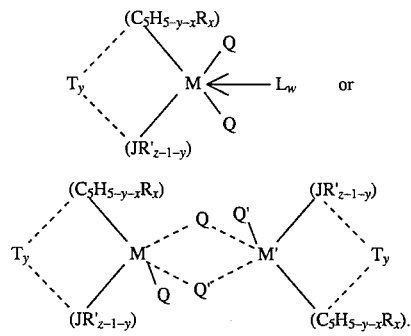

4. The catalyst system of claim 1 wherein the heteroatom ligand group J element is nitrogen, phosphorous, oxygen or sulfur.

5. The catalyst system of claim 1 wherein Q is a halogen or hydrocarbyl radical.

6. The catalyst system of claim 5 wherein the heteroatom ligand group J element is nitrogen.

7. The catalyst system of claim 1 wherein M is titanium.

8. The catalyst system of claim 1 wherein the aluminum atom to transition metal atom mole ratio is from about 10:1 to about 3,000:1.

9. The catalyst system of claim 1 further comprising an inert support.

10. The catalyst system of claim 9, wherein the support is an inorganic support selected from the group consisting of talc, silica, alumina, silica-alumina, magnesia, titania, zirconia, and mixtures thereof.

11. The catalyst system of claim 1, wherein E of said modifier is selected from the group consisting of carbon, silicon, nitrogen and phosphorous.

12. The catalyst system of claim 1, wherein G of said modifier is selected from the group consisting of oxygen, nitrogen, phosphorus and sulphur.

13. The catalyst system of claim 1, wherein said modifier is a compound reactive with aluminum alkyls.

14. The catalyst system of claim 1, wherein said modifier is a Lewis base or compound containing one or more Lewis basic functional groups.

15. The catalyst system of claim 1, wherein said modifier is a siloxane.

16. The catalyst system of claim 1, wherein said modifier is tetraethoxysilane, triphenylethoxysilane, diphenylethoxysilane or phenyltriethoxysilane.

17. The catalyst system of claim 1, wherein said modifier is N,N-dimethylanaline.

18. The catalyst system of claim 1, wherein said modifier is 2,6-di-t-butyl-4-methylphenol.

19. A catalyst system comprising:
(A) a transition metal compound of the formula:

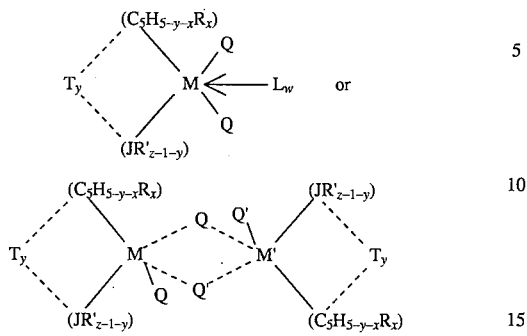

wherein
M is Zr, Hr, or Ti in its highest formal oxidation state;
$(C_5H_{5-y-x}R_x)$ is a cyclopentadienyl ring which is substituted with from zero to five substituent groups R, "x" is 0, 1, 2, 3, 4 or 5 denoting the degree of substitution, and each substituent group R is, independently, a radical selected from the group consisting of $C_1$–$C_{20}$ hydrocarbyl radicals; substituted $C_1$–$C_{20}$ hydrocarbyl radicals wherein one or more hydrogen atoms is replaced by a halogen radical, an amido radical, a phosphido radical, an alkoxy radical, an alkylborido radical, or other radical containing a Lewis acidic or basic functionality; $C_1$–$C_{20}$ hydrocarbyl-substituted metalloid radicals wherein the metalloid is selected from the Group IV A of the Periodic Table of Elements; halogen radicals; amido radicals; phosphido radicals; alkoxy radicals; alkylborido radicals; other radical containing a Lewis acidic or basic functionality; or $(C_5H_{5-y-x}R_x)$ is a cyclopentadienyl ring in which two adjacent R-groups are joined forming $C_4$–$C_{20}$ ring to give a saturated or unsaturated polycyclic cyclopentadienyl ligand;
$(JR'_{z-1-y})$ is a heteroatom ligand in which J is an element with a coordination number of three from Group V A or an element with a coordination number of two from Group VIA of the Periodic Table of Elements, each R' is, independently a radical selected from the group consisting of $C_1$–$C_{20}$ hydrocarbyl radicals and substituted $C_1$–$C_{20}$ hydrocarbyl radicals wherein one or more hydrogen atom is replaced by a halogen radical, an amido radical, a phosphido radical, an alkoxy radical, an alkylborido radical, or a radical containing a Lewis acidic or basic functionality; and "z" is the coordination number of the element J;
each Q is, independently, an univalent anionic ligand selected from the group consisting of halide, hydride, a substituted or unsubstituted $C_1$–$C_{20}$ hydrocarbyl, alkoxide, aryloxide, amide, arylamide, phosphide and arylphosphide, provided that where Q is a hydrocarbyl ligand Q cannot be a substituted or unsubstituted cyclopentadienyl ring or both Q together are an alkylidene, a cyclometallated hydrocarbyl or a divalent anionic chelating ligand;
"y" is 0 or 1 when "w" is greater than 0; "y" is 1 when "w" is 0; when "y" is 1, T is a covalent bridging group containing a Group III A, IV A, V A or VI A element;
L is a neutral Lewis base where "w" denotes a number from 0 to 3; and
(B) an alumoxane; and
(C) a modifier of the formula

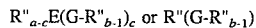

wherein G is a Group V A or VIA element and "b" is equal to the coordination number of G, E is a Group IV A or V A element and "a" is equal to the coordination number of E, "c" is an integer from 1 to 4 but not greater than a, and each R" is independently a hydrogen, hydrocarbyl or substituted hydrocarbyl radical.

20. The catalyst system of claim 19, wherein the heteroatom ligand group J element is nitrogen, phosphorous, oxygen or sulfur;
E of said modifier is carbon, silica, nitrogen or phosphorous; and
G of said modifier is oxygen, nitrogen, phosphorus or sulfur.

* * * * *